United States Patent [19]
Allen

[11] Patent Number: 5,959,118
[45] Date of Patent: Sep. 28, 1999

[54] PROCESS FOR THE PREPARATION OF 5-HYDROXYMETHYLTHIAZOLES

[75] Inventor: Michael S. Allen, Silver Lake, Wis.

[73] Assignee: Abbott Laboratories, Abbott Park, Ill.

[21] Appl. No.: 08/921,399

[22] Filed: Aug. 29, 1997

[51] Int. Cl.$^6$ ...................... C07D 277/22; C07D 277/24
[52] U.S. Cl. ............................................. 548/203; 548/202
[58] Field of Search ...................... 548/203, 202

[56] References Cited

U.S. PATENT DOCUMENTS

| | | | |
|---|---|---|---|
| 2,332,906 | 10/1943 | Foldi et al. | 260/302 |
| 3,299,083 | 1/1967 | Kollonitsch | 260/302 |
| 4,748,243 | 5/1988 | Beck et al. | 548/202 |
| 5,354,866 | 10/1994 | Kempf et al. | 546/265 |
| 5,541,206 | 7/1996 | Kempf et al. | 514/365 |
| 5,705,652 | 1/1998 | Jackson et al. | 548/202 |
| 5,712,400 | 1/1998 | Leanna et al. | 548/202 |
| 5,773,625 | 6/1998 | Langridge | 548/203 |
| 5,780,638 | 7/1998 | Kraus et al. | 548/203 |

FOREIGN PATENT DOCUMENTS

| | | |
|---|---|---|
| 19520612 | 12/1996 | Germany. |
| 19547076 | 6/1997 | Germany. |
| 9616050 | 5/1996 | WIPO. |
| 9710226 | 3/1997 | WIPO. |
| 9723469 | 7/1997 | WIPO. |
| 9832747 | 7/1998 | WIPO. |

OTHER PUBLICATIONS

Ahnoff et al., Analytical Chemistry 53 485–489 (1981).
Willy et al., Bull. Chem. Soc. 49 1989–1995 (1976).
Atherton et al., J. Am. Chem. Soc. Perkin I 528–546 (1981).
Al–Lohedan et al., J. Am. Chem. Soc. 104 6654–6660 (1982).
Land, et al., J. Org. Chem. 11 617–622 (1946) as cited in Beilsteins Handbuch der Organischen Chemie vol. 27, No. 4, p. 5414 (1984), XP002085655.
Naito, et al., Chem. Pharm. Bull. 39 2323–2332 (1991), XP–002085654.
English translation of German Patent Application No. DE19520612, publsihed Dec. 12, 1996.
Fallab, Helvetica Chimica Acta U35U 215–216 (1952) discloses a method for preparing 5–hydroxymethylthiazole by reducing the ethyl ester of thiazole–5–carboxylic acid.
Ashworth, et al., Organic Synthesis 4 128–129 (1963).

*Primary Examiner*—Laura L. Stockton
*Attorney, Agent, or Firm*—Steven R. Crowley

[57] ABSTRACT

The present invention discloses a process for the preparation of a hydroxymethylthiazole compound having formula 3:

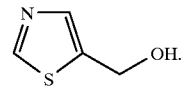

3

The process of the invention comprises reacting a halomethyl thiazole having the formula:

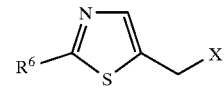

with water, at an elevated temperature. Optionally, the reaction can be carried out in the presence of a base, such as sodium carbonate, which can react with any acid formed. In the process of the invention, X is a halogen atom; and $R^6$ is selected from the group consisting of hydrogen, and halogen atoms. The invention also contemplates the preparation of acid addition salts of the hydroxymethylthiazole, compound 3.

11 Claims, No Drawings

PROCESS FOR THE PREPARATION OF 5-HYDROXYMETHYLTHIAZOLES

TECHNICAL FIELD

The present invention relates to a process for the preparation of substituted 5-hydroxymethylthiazoles which are useful as intermediates in the preparation of compounds that inhibit human immunodeficiency virus (HIV) protease.

BACKGROUND OF THE INVENTION

Compounds which are inhibitors of human immunodeficiency virus (HIV) protease are useful for inhibiting HIV protease in vitro and in vivo and are useful for inhibiting an HIV infection. Certain HIV protease inhibitors comprise a moiety which is a substituted 2,5-diamino-3-hydroxyhexane. HIV protease inhibitors of particular interest are compounds having formula 1:

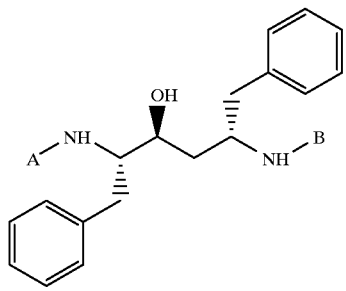

I wherein A is $R^2NHCH(R^1)C(O)$— and B is $R^{2a}$ or wherein A is $R^{2a}$ and B is $R^2NHCH(R^1)C(O)$— wherein $R^1$ is lower alkyl and $R^2$ and $R^{2a}$ are independently selected from —C(o)—$R^3$—$R^4$ wherein at each occurrence $R^3$ is independently selected from O, S and —N($R^5$)— wherein $R^5$ is hydrogen or lower alkyl and at each occurrence $R^4$ is independently selected from heterocyclic or (heterocyclic) alkyl; or a pharmaceutically acceptable salt, prodrug or ester thereof. Compounds of formula 1 are disclosed in U.S. Pat. No. 5,354,866, issued Oct. 11, 1994, and U.S. Pat. No. 5,541,206, issued Jul. 30, 1996.

A preferred HIV protease inhibitor having formula I is a compound of formula II:

or a pharmaceutically acceptable salt, prodrug or ester thereof. The compound having formula II is disclosed in U.S. Pat. No. 5,421,206, issued Jul. 30, 1996 (the '206 patent).

An intermediate which is especially useful for preparing compounds having formula II is a compound having the formula 3 or an acid addition salt thereof:

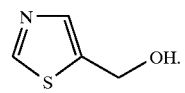

3

The preparation of compounds having formula 3 has been disclosed in the '206 patent and International Patent Application No. WO 96/16050 published May 30, 1996 (the '050 application).

Methods for the preparation of 5-hydroxymethylthiazole disclosed in U.S. Pat. No. 5,541,206 include those shown in Scheme 1. However, neither of these methods is suited for large scale production of pure 5-hydroxymethylthiazole.

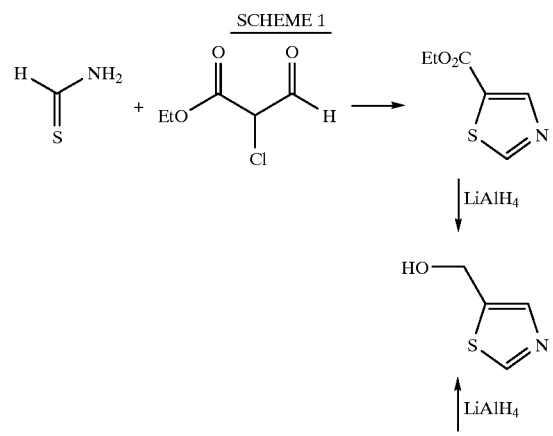

SCHEME 1

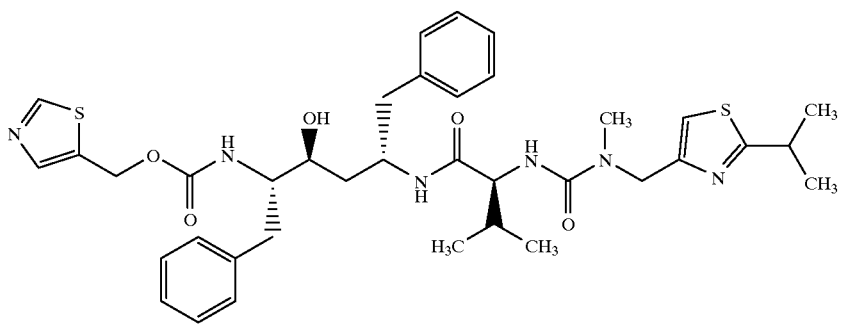

II

3

-continued

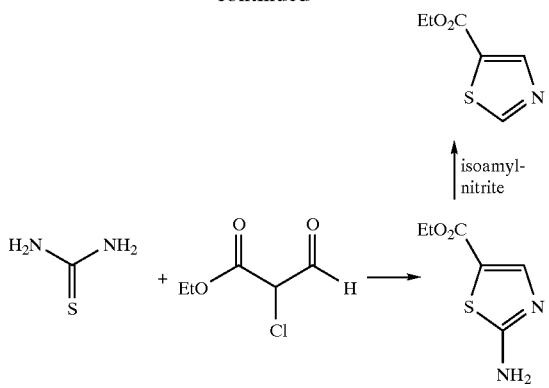

The '050 application discloses a preparation in which 2-chloro-5-chloro-methylthiazole is reacted with a carboxylic acid salt in the presence of a phase transfer catalyst. This provides an ester which is then hydrolyzed to provide 2-chloro-5-hydroxymethylthiazole. Dechlorination of the chloroalcohol is then accomplished by catalytic hydrogenation. Drawbacks which occur when using this method are the additional hydrolysis step required to obtain the alcohol and difficulties in removing the quaternary ammonium phase transfer catalyst.

Thus, there is a continuing need for improved processes for the preparation of 5-hydroxymethylthiazoles.

SUMMARY OF THE INVENTION

All patents, patent applications, and literature references cited in the specification are hereby incorporated by reference in their entirety. In the case of inconsistencies, the present disclosure, including definitions, will prevail.

The present invention discloses a process for the preparation of a compound having formula 3 or an acid addition salt thereof:

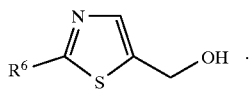

The process of the invention comprises reacting a halomethyl thiazole having the formula:

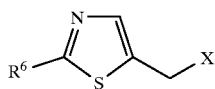

with water, at an elevated temperature. Optionally, the reaction can be carried out in the presence of a base, such as sodium carbonate, which can react with any acid formed. In the process of the invention, X is a halogen atom; and $R^6$ is selected from the group consisting of hydrogen, and halogen atoms. The invention also contemplates the preparation of acid addition salts of compound 3.

Examples of suitable bases include but are not limited to weak bases like, carbonates or bicarbonates such as, for example sodium carbonate, potassium carbonate, ammonium carbonate, sodium bicarbonate, potassium bicarbonate ammonium bicarbonate, and the like; ammonium hydroxide, water soluble weakly nucleophilic bases such as, for example, triethylamine, and the like. The carbonate bases can have a mono- or multivalent cation. Preferred cations are alkali metal ions such as, for example, sodium, potassium and the like. A preferred base is sodium carbonate.

The process of the invention is illustrated in Scheme II. In the process the halide, X, is replaced with a hydroxyl group. The preferred temperature for the displacement reaction is from about 20° C. to about 100° C. and preferably from about 70° C. to about 80° C. The reaction time is from about 1 hour to about 8 hours and preferably from about 2 hours to about 3 hours.

The amount of water required is typically from about 1 mL/g of thiazole to about 50 mL/g of thiazole and preferably from about 5 mL/g of thiazole to about 15 mL/g of thiazole.

Dechlorination of 2-chloro-5-hydroxymethylthiazole (for example, by catalytic hydrogenation, reaction with zinc/acetic acid, or reaction with hydrogen gas and a palladium catalyst, and the like) provides 5-hydroxymethylthiazole.

Preferably, 5-hydroxymethylthiazole is prepared according to the process illustrated in Scheme II, starting from 2-chloro-5-chloromethylthiazole ($R^6$ and X are chlorine). This compound can be prepared as described in U.S. Pat. No. 4,748,243. The 2-chloro-5-chloromethylthiazole is reacted with water according to the process of the invention to provide 2-chloro-5-hydroxymethylthiazole which can be dechlorinated, e.g., via catalytic hydrogenation, to provide 5-hydroxymethylthiazole.

SCHEME 2

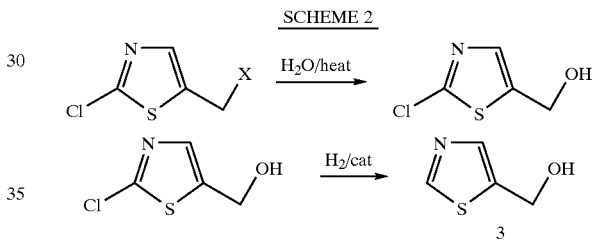

Catalytic hydrogenation is a preferred method for dechlorination. The catalytic hydrogenation of 2-chloro-5-hydroxymethylthiazole can be accomplished using hydrogen at a pressure of from about 1 atmosphere to about 10 atmospheres, and a hydrogenation catalyst (e.g., Pd/C, RaNi, and the like) in the amount of from about 1% to about 25% (by weight) in an inert solvent (e.g., methanol, ethanol, and the like).

In practicing the present invention, the halogen atoms are selected from the group consisting of fluorine, chlorine, bromine and iodine. The preferred halogen atoms are chlorine and bromine.

The term "acid addition salts", as used herein, are salts of an amino group formed with inorganic acids such as hydrochloric acid, hydrobromic acid, phosphoric acid, sulfuric acid perchloric acid, and the like, or with organic acids such as acetic acid, oxalic acid, maleic acid, tartaric acid, citric acid, succinic acid, malonic acid, and the like, or by using other methods used in the art such as ion exchange.

The reagents required for the synthesis of the compounds of the invention are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA); Alfa Aesar (Ward Hill, Mass. 01835-9953); Eastman Chemical Company (Rochester, N.Y. 14652-3512); Lancaster Synthesis Inc. (Windham, N.H. 03087-9977); Spectrum Chemical Manufacturing Corp. (Janssen Chemical) (New Brunswick, N.J. 08901); Pfaltz and Bauer (Waterbury, Conn. 06708). Compounds which are not commercially available can be prepared by employing known methods from the chemical literature.

The following examples illustrate the process of the invention, without limitation.

EXAMPLE 1

2-Chloro-5-Hydroxymethylthiazole (2-Cl-5-HMT)

2-Chloro-5-chloromethylthiazole hydrochloride (10 g, 0.049 mole) and water (100 mL) were charged to a flask. The resultant mixture was stirred at 80° C. for up to but not more than 3 hours. The reaction mixture (about pH =1) was then cooled to room temperature and 10% aqueous sodium carbonate was added was added to raise the pH of the solution to about 8–9. The product was extracted with methyl t-butyl ether (2×100 mL). The combined organic extracts were dried over $Na_2SO_4$ (about 10 g) and stirred for 45 minutes. Optionally, decolorizing carbon can be used. (If a good azeodrying solvent such as ethyl acetate is employed as the extraction solvent a drying agent such as $Na_2SO_4$ is unnecessary.) The solution was then filtered through a fritted glass funnel and the filtrates were concentrated to a yellow colored oil under reduced pressure to provide 2-chloro-5-hydroxymethylthiazole: 5.65 g, 77.3%.

EXAMPLE 2

2-Chloro-5-Hydroxymethylthiazole (2-Cl-5-HMT)

2-Chloro-5-chloromethylthiazole 14.5 g, (0.086 mole) and water (140 mL) were charged to a flask. The resultant mixture was stirred at 80° C. for up to but not more than 3 hours. The reaction mixture (about pH=1) was then cooled to room temperature and solid sodium carbonate was added to raise the pH of the solution to about 8–9. The product was extracted with ethyl acetate (2×150 mL). The combined organic extracts were dried over $Na_2SO_4$ (about 20 g) and stirred for 45 minutes with 2.0 g of decolorizing carbon (Norit® AS-3 about 100 mesh). The solution was then filtered through a fritted glass funnel and the filtrates were concentrated to a light yellow colored oil under reduced pressure to provide 2-chloro-5-hydroxymethylthiazole. Yield 12.51 g; 97%.

Results are illustrated below.

$^1$H NMR (CDCl$_3$) δ3.9 (s, broad, 1H), 4.79 (s, 2H), 7.35 (s, 1H).

MS(Cl) m/e 150 (M+H)$^+$, 167 (M+NH$_4$)$^+$.

EXAMPLE 3

2-Chloro-5-Hydroxymethylthiazole Hydrochloride

2-Chloro-5-chloromethylthiazole hydrochloride (100 g, 0.49 mole), and water (100 mL) were charged to a flask. The mixture was stirred and heated to 80° C. for 2.5 hours. The reaction mixture was cooled to about 15° C. and sodium carbonate (51.5 g) was added (to raise the pH to about 8–9). The product was extracted with ethyl acetate (1×500 mL and 1×250 mL). The combined organic extracts were stirred for 20 minutes with 3 g of decolorizing carbon (Norit® SA3 about 100 mesh) and filtered through celite. The celite and flask were washed with an additional 100 mL of ethyl acetate and combined with the filtrate. The filtrate was concentrated under reduced pressure to provide a yellow-orange oil. The oil was dissolved in 500 mL of ethyl acetate and cooled to −10° C., under a nitrogen atmosphere. A solution of HCl (17.82 grams, 1 eq.) in ethyl acetate was slowly added. The temperature was maintained below −5° C. After the addition was complete the slurry formed was stirred for 30 minutes. The product was filtered under vacuum and the flask and product washed with ethyl acetate (100 mL). The title compound, an off white powder, was purged with nitrogen gas until dry. Yield 63.3 g; 69.6%..

Results are illustrated below.

$^1$H NMR (CDCl$_3$) δ 4.3 (s, broad, 1 H), 4.83 (s, 2H), 7.45 (s, 1H).

MS(Cl) m/e 150 (M+H)$^+$, 167 (M+NH$_4$)$^+$.

EXAMPLE 4

Preparation of 5-Hydroxymethylthiazole

2-Chloro-5-hydroxymethylthiazole (74.0 g, 495 mmol), was dissolved in methanol (925 mL) and charged into a Parr shaker. To this solution was charged sodium carbonate (26.76 g, 252.5 mmol, 0.51 eq) and 10% palladium on carbon (11.1 g). The system was heated (60° C.) under 50 psi (3.40 atm) of hydrogen gas and agitated for 8 hours. (The reaction mixture can be vented periodically to release the buildup of carbon dioxide gas). The shaker was then cooled and the contents filtered through a bed of diatomaceous earth. The filtrate was then concentrated under reduced pressure (38° C.) and the residue was taken up in methyl t-butyl ether (600 mL) and dried over sodium sulfate (70 g). The dried solution was filtered and concentrated under reduced pressure (38° C.) to provide 5-hydroxymethylthiazole. Yield 52.2 g, 91.6%.

Results are illustrated below.

$^1$H NMR (CDCl$_3$) δ 2.9 (broad s, 1H), 4.85 (s, 2H), 7.67 (d, 1H), 8.70 (s, 1H).

MS (Cl) m/e 116 (M+H)$^+$, 133 (M+NH$_4$)$^+$.

EXAMPLE 5

Preparation of 5-Hydroxymethylthiazole

2-Chloro-5-hydroxymethylthiazole hydrochloride (3.72 g, 0.02 mole), was dissolved in methanol (30 mL) and charged into a Parr shaker. To this solution was charged sodium carbonate (2.12 g, 0.02 mole) and 10% palladium on carbon (0.9 g). The system was heated (60° C.) under 50 psi (3.40 atm) of hydrogen gas and agitated for 18 hours. The reaction was monitored by TLC or GC and allowed to proceed for an additional 5 hours after completion. The reaction mixture was cooled and the contents filtered through a bed of diatomaceous earth. The filtrate was then concentrated under reduced pressure (38° C.) and the residue was taken up in methyl t-butyl ether (100 mL) and dried over sodium sulfate (10 g). The dried solution was filtered and concentrated under reduced pressure (38° C.) to provide 5-hydroxymethylthiazole as a slightly colored oil. Yield 2.05 g, 89.1%. The NMR and mass spectral data were identical to the 5-hydroxymethylthiazole product prepared in Example 4.

EXAMPLE 6

Preparation of 5-Hydroxymethylthiazole

2-Chloro-5-hydroxymethylthiazole hydrochloride (3.0 g, 0.02 mole), was dissolved in methanol (30 mL) and charged into a Parr shaker. To this solution was charged triethyl amine (4.09 g, 0.04 mole) and 10% palladium on carbon (0.45 g). The system was heated (57° C.) under 58.8 psi (4.0 atm) of hydrogen gas and agitated for 18 hours. The reaction was monitored by TLC or GC and allowed to proceed for an additional 5 hours after completion. The reaction mixture was cooled and the contents filtered through a bed of diatomaceous earth. The filtrate was then concentrated under reduced pressure and the residue was taken up in methyl t-butyl ether (60 mL) and dried over sodium sulfate (5 g). The dried solution was filtered and concentrated under reduced pressure to provide 5-hydroxymethylthiazole as a slightly colored oil. Yield 2.1 g, 91.3 %. The NMR and mass spectral data were identical to the 5-hydroxymethylthiazole product prepared in Example 4.

The foregoing is merely illustrative of the invention and is not intended to limit the invention to the disclosed processes and reaction conditions. Variations which are obvious to one of ordinary skill in the art are intended to be included within the scope and nature of the invention which are defined in the appended claims.

What is claimed is:

1. A process for the preparation of a compound having the formula:

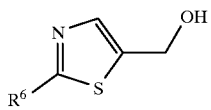

or an acid addition salt thereof, said process comprising the step of reacting a halomethyl thiazole having the formula:

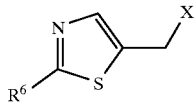

or an acid addition salt thereof with water; wherein X is a halogen atom; and $R^6$ is a halogen atom.

2. The process according to claim 1 wherein $R^6$ is a halogen atom selected from chlorine, bromine and iodine.

3. The process according to claim 1 wherein $R^6$ is chlorine or bromine.

4. The process according to claim 1 wherein X is a halogen atom selected from chlorine, bromine and iodine.

5. The process according to claim 1 wherein X is chlorine or bromine.

6. The process according to claim 1 wherein the halomethylthiazole compound is 2-chloro-5-chloromethylthiazole or an acid addition salt thereof.

7. The process according to claim 1 wherein the halomethylthiazole compound is 2-bromo-5-chloromethylthiazole or an acid addition salt thereof.

8. The process according to claim 1 wherein the halomethylthiazole compound is 2-chloro-5-bromomethylthiazole or an acid addition salt thereof.

9. The process according to claim 1 further comprising the step of dehalogenating the 2-halo-5-hydroxymethylthiazole compound.

10. The process according to claim 1 wherein the 2-halo-5-hydroxymethylthiazole compound is 2-bromo-5-hydroxythiazole.

11. The process according to claim 9 wherein the 2-halo-5-hydroxymethylthiazole compound is 2-chloro-5-hydroxythiazole.

* * * * *

UNITED STATES PATENT AND TRADEMARK OFFICE
CERTIFICATE OF CORRECTION

PATENT NO. : 5,959,118
DATED : September 28, 1999
INVENTOR(S) : Michael S. Allen It is certified that error appears in the above-identified patent and that said Letters Patent is hereby corrected as shown below:

Col. 8, line 28   delete "1"  insert --9--

Signed and Sealed this

Twentieth Day of June, 2000

Attest:

Attesting Officer

Q. TODD DICKINSON
Director of Patents and Trademarks